(12) United States Patent
Wang et al.

(10) Patent No.: US 8,592,634 B2
(45) Date of Patent: *Nov. 26, 2013

(54) PROCESS FOR PRODUCING PHENOL

(75) Inventors: Kun Wang, Bridgewater, NJ (US); Francisco M. Benitez, Houston, TX (US); James R. Lattner, Laporte, TX (US); Jihad M. Dakka, Whitehouse Station, NJ (US); Edmund J. Mozeleski, Califon, NJ (US); Stephen Zushma, Clinton, NJ (US)

(73) Assignee: ExxonMobil Chemical Patents Inc., Houston, TX (US)

( * ) Notice: Subject to any disclaimer, the term of this patent is extended or adjusted under 35 U.S.C. 154(b) by 170 days.

This patent is subject to a terminal disclaimer.

(21) Appl. No.: 13/143,975

(22) PCT Filed: Jan. 25, 2010

(86) PCT No.: PCT/US2010/021949
§ 371 (c)(1),
(2), (4) Date: Aug. 16, 2011

(87) PCT Pub. No.: WO2010/098916
PCT Pub. Date: Sep. 2, 2010

(65) Prior Publication Data
US 2011/0301387 A1    Dec. 8, 2011

Related U.S. Application Data

(60) Provisional application No. 61/155,746, filed on Feb. 26, 2009.

(51) Int. Cl.
*C07C 37/08*    (2006.01)

(52) U.S. Cl.
USPC .......................................... 568/798

(58) Field of Classification Search
USPC .......................................... 568/798
See application file for complete search history.

(56) References Cited

U.S. PATENT DOCUMENTS

| | | | |
|---|---|---|---|
| 3,821,314 A | 6/1974 | Arkell et al. | |
| 3,959,381 A | 5/1976 | Arkell et al. | |
| 4,021,490 A | 5/1977 | Hudson | |
| 4,230,638 A | 10/1980 | Murtha | |
| 4,262,151 A | 4/1981 | Pujado | |
| 4,358,618 A | 11/1982 | Sifniades et al. | |
| 4,480,141 A | 10/1984 | Drake | |
| 4,482,757 A | 11/1984 | Drake | |
| 4,487,970 A | 12/1984 | Drake | |
| 4,490,565 A | 12/1984 | Chang et al. | |
| 4,490,566 A | 12/1984 | Chang et al. | |
| 4,568,769 A * | 2/1986 | Yashima et al. | 568/342 |
| 4,870,217 A | 9/1989 | Knifton | |
| 4,898,995 A | 2/1990 | Knifton et al. | |
| 5,254,751 A | 10/1993 | Zakoshansky | |
| 6,037,513 A | 3/2000 | Chang et al. | |
| 6,169,215 B1 | 1/2001 | Levin et al. | |
| 6,284,927 B1 | 9/2001 | Druliner et al. | |
| 6,720,462 B2 | 4/2004 | Kuhnle et al. | |
| 6,852,893 B2 | 2/2005 | Kuhnle et al. | |
| 2003/0083527 A1 | 5/2003 | Kuhnle et al. | |
| 2004/0162446 A1 | 8/2004 | Black | |
| 2004/0236152 A1 | 11/2004 | Black et al. | |
| 2007/0265476 A1 | 11/2007 | Dakka et al. | |

FOREIGN PATENT DOCUMENTS

| | | |
|---|---|---|
| EP | 0 492 807 | 7/1992 |
| GB | 681613 | 10/1952 |
| WO | 2006/015826 | 2/2006 |
| WO | 2008/128638 | 10/2008 |

OTHER PUBLICATIONS

Aoki et al., "*One-Pot Synthesis of Phenol and Cyclohexanone From Cyclohexylbenzene Catalyzed by N-Hydroxyphthalimide (NHPI)*", Tetrahedron, 2005, vol. 61, pp. 5219-5222.
Knifton et al., "*Phenol/Acetone Cogeneration Via Solid Acid Catalysis*", Applied Catalysis A: General, 1997, vol. 161, pp. 199-211.
Maksimov et al., "$WO_3/MO_2$ ($M=Zr$, $Sn$, $Ti$) *Heterogeneous Acid Catalysts: Synthesis, Study, and Use in Cumene Hydroperoxide Decomposition*", Kinetics and Catalysis, 2006, vol. 47, No. 4, pp. 564-571.
Schmidt et al., "*New Developments in the Sunoco/UOP Phenol Technology*", presented at the AICHE Spring Meeting (Apr. 2004), New Orleans, LA.
Selvin et al., "*Catalytic Decomposition of Cumene Hydroperoxide Into Phenol and Acetone*", Applied Catalysis A: General, 2001, vol. 219, pp. 125-129.
Zakoshansky, "*Acid-catalytic Cumene Hydroperoxide Cleavage Process in Boiling Acetone Medium*", presented at the AICHE Spring Meeting (Mar. 2002), New Orleans, LA.

* cited by examiner

*Primary Examiner* — Brian J Davis
(74) *Attorney, Agent, or Firm* — Jamie L. Sullivan; Siwen Chen

(57) ABSTRACT

Disclosed is a process for producing phenol or a substituted phenol and a co-product comprising the steps of (i) contacting a first stream comprising an alkylaromatic compound with a second stream comprising an oxygen-containing gas in the presence of a first catalyst comprising a cyclic imide under conditions to convert at least a portion of said alkylaromatic compound to an alkylaromatic hydroperoxide, (ii) producing an effluent stream comprising said cyclic imide, said alkylaromatic hydroperoxide, and said alkylaromatic compound wherein said effluent stream has an alkylaromatic hydroperoxide concentration of from 10 to 40 wt %; and (iii) contacting in a second reactor at least a portion of said effluent stream with a second catalyst to convert said alkylaromatic hydroperoxide to a product stream comprising phenol and said co-product.

25 Claims, No Drawings

PROCESS FOR PRODUCING PHENOL

CROSS REFERENCE TO RELATED APPLICATIONS

This application is a National Stage Application of International Application No. PCT/US2010/021949 filed Jan. 25, 2010, which claims the benefit of prior U.S. Provisional Application Ser. No. 61/155,746 filed Feb. 26, 2009 both of which are hereby incorporated by reference in their entirety.

FIELD

The present invention relates to a process for producing phenol or a substituted phenol and a co-product.

BACKGROUND

Phenol is an important product in the chemical industry. For example, phenol is useful in the production of phenolic resins, bisphenol A, ε-caprolactam, adipic acid, alkyl phenols, and plasticizers.

Currently, the most common route for the production of phenol is the Hock process. This is a three-step process in which the first step involves alkylation of benzene with propylene to produce cumene, an alkylaromatic compound in the presence of an acidic catalyst. The second step is the oxidation, preferably aerobic oxidation of cumene to the corresponding cumene hydroperoxide. The third step is the cleavage of the cumene hydroperoxide in the presence of heterogeneous or homogenous catalysts into equimolar amounts of phenol and acetone, a co-product. However, the world demand for phenol is growing more rapidly than that for the acetone co-product. In addition, due to developing shortages in supply, the cost of propylene is likely to increase.

Thus, a process that avoids or reduces the use propylene as a feed and coproduces higher ketones, such as methyl ethyl ketone and/or cyclohexanone, rather than acetone may be an attractive alternative route to the production of phenol. For example, methyl ethyl ketone is in demand for use as a lacquer and a solvent and for dewaxing of lubricating oils. In addition, there is a growing market for cyclohexanone, which is used as an industrial solvent, as an activator in oxidation reactions and in the production of adipic acid, cyclohexanone resins, cyclohexanone oxime, caprolactam and nylon 6.

It is known that phenol and methyl ethyl ketone can be co-produced by a variation of the Hock process in which sec-butylbenzene is oxidized to obtain sec-butylbenzene hydroperoxide and the hydroperoxide is decomposed to the desired phenol and methyl ethyl ketone. The sec-butylbenzene can be produced by alkylation of benzene with linear butenes over zeolite beta or a molecular sieve of the MCM-22 family. Details of such a process can be found in, for example, International Patent Publication No. WO2006/015826.

Similarly, U.S. Pat. No. 6,037,513 discloses that cyclohexylbenzene can be produced by contacting benzene with hydrogen in the presence of a bifunctional catalyst comprising a molecular sieve of the MCM-22 family and at least one hydrogenation metal selected from palladium, ruthenium, nickel, cobalt and mixtures thereof. The '513 patent also discloses that the resultant cyclohexylbenzene can be oxidized to the corresponding hydroperoxide which is then decomposed to the desired phenol and cyclohexanone co-product.

In the commercial Hock process, the dilute cumene hydroperoxide from the oxidation step is first concentrated to greater than 80% under vacuum, which is then sent to the cleavage reactor. In addition to the hazards associated with handling concentrated hydroperoxide, cleavage of concentrated hydroperoxide also poses safety concerns due to the rapid and highly exothermic nature of the reaction. Further, significant amounts of side products may also form from the concentrated oxidation products. In practice, the concentrated cumene hydroperoxide is often diluted with solvents such as acetone in order to better manage the reaction heat and to control by-product formation.

In the case of cyclohexylbenzene oxidation, another disadvantage of concentrating cyclohexylbenzene hydroperoxide exists. Due to the very high boiling point of cyclohexylbenzene, high vacuum and high temperature are required in order to remove cyclohexylbenzene and concentrate cyclohexylbenzene hydroperoxide, which may lead to undesired decomposition of cyclohexylbenzene hydroperoxide.

In addition, the production of phenol using sec-butylbenzene and/or cyclohexylbenzene as the alkylbenzene precursor is accompanied by certain problems which either is not present or is less severe with a cumene-based process. For example, in comparison to cumene, oxidation of sec-butylbenzene and cyclohexylbenzene to the corresponding hydroperoxide is very slow in the absence of a catalyst and is very sensitive to the presence of impurities. As a result, U.S. Pat. Nos. 6,720,462 and 6,852,893 have proposed the use of cyclic imides, such as N-hydroxyphthalimide, as catalysts to facilitate the oxidation of alkylbenzenes, such as sec-butylbenzene and cyclohexylbenzene.

All of these problems increase the complexity and investment involved in the cleavage process and hence various alternatives have been proposed.

The synthesis of phenol and cyclohexanone in one pot with selectivities of 96% and 91%, respectively, at 25% conversion, by means of aerobic oxidation of cyclohexylbenzene in the presence of the N-hydroxyphthalimide, followed by treatment with sulfuric acid, as disclosed by Aoki et al. in *Tetrahedron*, Vol. 61 pages 5219-5222 (2005).

According to the present invention, it has now been found that cleavage of hydroperoxides directly out of the oxidization reactor may be achieved without the need of first concentrating the hydroperoxides. The un-reacted alkyl benzenes act as diluents for the peroxides, which can help manage the heat of cleavage reaction and better control formation of heavy by-products. Phenol and co-products are produced with selectivities of greater than or equal to 98%.

SUMMARY

In one aspect, the invention disclosed is a continuous process for producing phenol or a substituted phenol and a co-product, the process comprising the steps of:

(a) contacting in a first reactor a first stream comprising an alkylaromatic compound with a second stream comprising an oxygen-containing gas in the presence of a first catalyst comprising a cyclic imide under conditions to convert at least a portion of said alkylaromatic compound to an alkylaromatic hydroperoxide, wherein said alkylaromatic compound having a general formula (II):

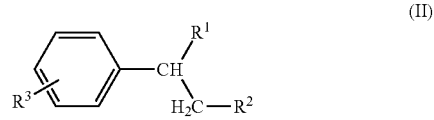

(II)

in which $R^1$ and $R^2$ each independently represents an alkyl group having from 1 to 4 carbon atoms, provided that $R^1$ and $R^2$ may be joined to form a cyclic group having from 4 to 10 carbon atoms, said cyclic group being optionally substituted, and $R^3$ represents hydrogen, one or more alkyl groups having from 1 to 4 carbon atoms or a cyclohexyl group,
wherein said cyclic imide having a general formula (III):

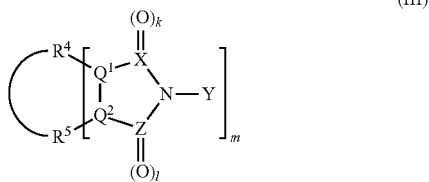

(III)

in which each of $R^4$ and $R^5$ is independently selected from hydrocarbyl and substituted hydrocarbyl radicals having 1 to 20 carbon atoms, or from the groups $SO_3H$, $NH_2$, OH, and $NO_2$ or from the atoms H, F, Cl, Br, and I, provided that $R^4$ and $R^5$ can be linked to one another via a covalent bond, each of $Q^1$ and $Q^2$ is independently selected from C, CH, N, $CR^6$, each of X and Z is independently selected from C, S, $CH_2$, N, P and elements of Group 4 of the Periodic Table of Elements, Y is O or OH, k is 0, 1, or 2, l is 0, 1, or 2;
m is 1 to 3; and $R^6$ can be any of the entities listed for $R^4$, and wherein said alkylaromatic hydroperoxide having a general formula (I):

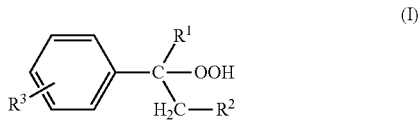

(I)

in which each of $R^1$, $R^2$ and $R^3$ is as defined above;
(b) producing an effluent stream comprising said cyclic imide, said alkylaromatic hydroperoxide, and said alkylaromatic compound wherein said effluent stream has an alkylaromatic hydroperoxide concentration of from 10 to 40 wt % (weight %); and
(c) contacting in a second reactor at least a portion of said effluent stream with a second catalyst to convert said alkylaromatic hydroperoxide to a product stream comprising phenol and said co-product.

In one embodiment, at least part of said cyclic imide is removed from the effluent by contacting said effluent stream.

In another embodiment, the effluent stream is not substantially concentrated prior to said contacting (c).

In another embodiment, at least part of said cyclic imide is removed by contacting said effluent stream with a solid sorbent. Conveniently, said solid sorbent comprises a metal oxide, a metal carbonate and/or hydrogen carbonate, a clay, and/or an ion exchange resin.

Conveniently, said cyclic imide having the general formula (IV):

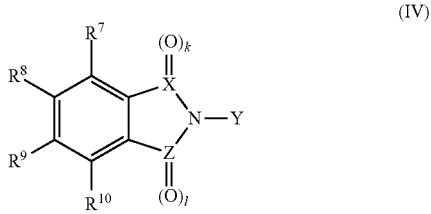

(IV)

wherein each of $R^7$, $R^8$, $R^9$, and $R^{10}$ is independently selected from hydrocarbyl and substituted hydrocarbyl radicals having 1 to 20 carbon atoms, or from the groups $SO_3H$, $NH_2$, OH, and $NO_2$ or from the atoms H, F, Cl, Br, and I, each of X and Z is independently selected from C, S, $CH_2$, N, P and elements of Group 4 of the Periodic Table of Elements, Y is O or OH, k is 0, 1, or 2, and l is 0, 1, or 2.

In one embodiment, said cyclic imide comprises N-hydroxyphthalimide.

These cyclic imides can be used either alone or in the presence of a free radical initiator and can be used as liquid-phase, homogeneous catalysts or can be supported on a solid carrier to provide a heterogeneous catalyst. Typically, the N-hydroxy substituted cyclic imide is employed in an amount between 0.0001 wt % to 15 wt %, such as between 0.001 wt % to 5 wt %, 0.01 wt % to 3 wt %, 0.05 wt % to 0.5 wt %, 0.01 wt % to 0.2 wt %, 0.1 wt % to 1 wt % of the cyclohexylbenzene. In one embodiment, the cyclic imide catalyst is added to the oxidation reaction step by dissolving in either the cyclohexylbenzene feed or in the reaction media (or a combination). The catalyst is advantageously added to the reaction media, where the temperature is already high, and where there is present some hydroperoxide, both of which contribute to the improved solubility of the solid catalyst.

In one embodiment, the phenol yield is greater than or equal to about 0.90, preferably greater than or equal to about 0.93, more preferably greater than or equal to about 0.96, most preferably greater than or equal to about 0.98.

In another embodiment, said alkylaromatic compound is sec-butylbenzene, said alkylaromatic hydroperoxide is sec-butylbenzene hydroperoxide and said co-product is methyl ethyl ketone. Conveniently, the methyl ethyl ketone yield is greater than or equal to about 0.90, preferably greater than or equal to 0.93, more preferably greater than or equal to 0.96, most preferably greater than or equal to 0.98.

In another embodiment, said alkylaromatic compound is cyclohexylbenzene, said alkylaromatic hydroperoxide is cyclohexylbenzene hydroperoxide and said co-product is cyclohexanone. Conveniently, the cyclohexanone yield is greater than or equal to about 0.90, preferably greater than or equal to 0.93, more preferably greater than or equal to 0.96, most preferably greater than or equal to 0.98.

In another embodiment, said alkylaromatic compound is cyclohexylbenzene and 1,2- or 1,3-methylcyclopentylbenzene (0-50 wt %); said alkylaromatic hydroperoxide is cyclohexylbenzene hydroperoxide and 1,2- or 1,3-methylcyclopentyl benzene peroxide; and said co-product is cyclohexanone and 2- or 3-methylcyclopentanone.

In another embodiment, said alkylaromatic compound is 1,2- or 1,3-methylcyclopentylbenzene, said alkylaromatic hydroperoxide is 1,2- or 1,3-methylcyclopentyl benzene peroxide, and said co-product is 2- or 3-methylcyclopentanone.

DETAILED DESCRIPTION OF THE EMBODIMENTS

Disclosed is a process for producing phenol or a substituted phenol and a co-product comprising the steps of (i) contacting in a first reactor a first stream comprising an alkylaromatic compound with a second stream comprising an oxygen-containing gas in the presence of a first catalyst comprising a cyclic imide under conditions to convert at least a portion of said alkylaromatic compound to an alkylaromatic hydroperoxide, (ii) producing an effluent stream comprising said cyclic imide and said alkylaromatic hydroperoxide wherein said effluent stream has an alkylaromatic hydroperoxide concentration of from 10 to 40 wt % (weight %); and (iii) contacting in a second reactor said effluent stream with a second catalyst to convert said alkylaromatic hydroperoxide to a product stream comprising phenol and said co-product.

Preferably, the disclosed process is continuous; however, batchwise processes are contemplated.

Said alkylaromatic compound has a general formula (II):

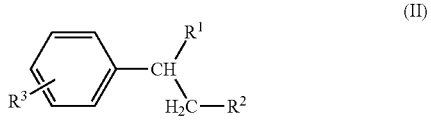

in which $R^1$ and $R^2$ each independently represents an alkyl group having from 1 to 4 carbon atoms, provided that $R^1$ and $R^2$ may be joined to form a cyclic group having from 4 to 10 carbon atoms, said cyclic group being optionally substituted, and $R^3$ represents hydrogen, one or more alkyl groups having from 1 to 4 carbon atoms or a cyclohexyl group.

Said cyclic imide has a general formula (III):

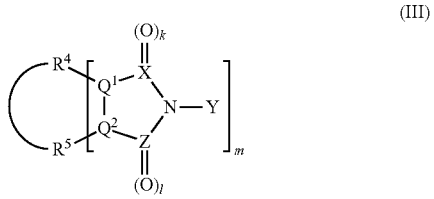

in which each of $R^4$ and $R^5$ is independently selected from hydrocarbyl and substituted hydrocarbyl radicals having 1 to 20 carbon atoms, or from the groups $SO_3H$, $NH_2$, $OH$, and $NO_2$ or from the atoms H, F, Cl, Br, and I, provided that $R^4$ and $R^5$ can be linked to one another via a covalent bond, each of $Q^1$ and $Q^2$ is independently selected from C, CH, N, $CR^6$, each of X and Z is independently selected from C, S, $CH_2$, N, P and elements of Group 4 of the Periodic Table of Elements, Y is O or OH, k is 0, 1, or 2, l is 0, 1, or 2; m is 1 to 3; and $R^6$ can be any of the entities listed for $R^4$.

Said alkylaromatic hydroperoxide has a general formula (I):

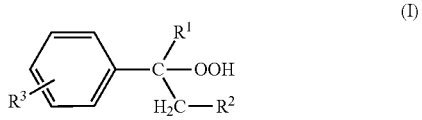

in which each of $R^1$, $R^2$ and $R^3$ is as defined above in general formula (III).

Examples of suitable alkylaromatic compounds which are made into their corresponding hydroperoxides include cumene, sec-butylbenzene, p-methyl-sec-butylbenzene, 1,4-diphenylcyclohexane, sec-pentylbenzene, sec-hexylbenzene, cyclopentylbenzene, cyclohexylbenzene and cyclooctylbenzene. Preferred alkylaromatic hydroperoxides of general formula (I) include cumene hydroperoxide, sec-butylbenzene hydroperoxide and cyclohexylbenzene hydroperoxide.

For example, cyclohexylbenzene may be produced by the hydroalkylation of benzene in presence of bifunctional catalyst comprising an MCM-22 family molecular sieve and a hydrogenation metal, such as described in U.S. Pat. No. 6,037,513. In addition to cyclohexylbenzene, benzene hydroalkylation also produces by-products such as cyclohexane; methylcyclopentane; dicyclohexylbenzenes; and different isomers of methylcyclopentylbenzene including 1,2- and 1,3-methylcyclopentylbenzene. Conveniently, 1,2- and 1,3-methylcyclopentylbenzene may be converted to phenol and 2- and 3-methylcyclopentanone by the oxidation and cleavage steps described herein.

Production of Alkylaromatic Hydroperoxides

The alkylaromatic hydroperoxides employed in the present process are typically produced by the catalyzed oxidation of an alkylaromatic compound having the general formula (II):

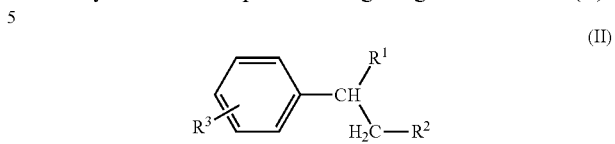

wherein $R^1$, $R^2$ and $R^3$ have the meanings ascribed in the above definition of general formula (III). The alkylaromatic precursor compound is in turn produced by known aromatic alkylation processes. For example, sec-butylbenzene hydroperoxide is conveniently produced by oxidation of the sec-butylbenzene product resulting from the alkylation of benzene with linear butenes in presence of an MCM-22 family catalyst, such as described in International Patent Publication No. WO2006/015826. Similarly, cyclohexylbenzene hydroperoxide is conveniently produced by oxidation of the cyclohexylbenzene product resulting from the hydroalkylation of benzene in presence of bifunctional catalyst comprising an MCM-22 family molecular sieve and a hydrogenation metal, such as described in U.S. Pat. No. 6,037,513. Similar processes can be used to produce the other hydroperoxides that can be employed in the present process.

The oxidation process employed in the production of the desired hydroperoxide generally involves reacting the alkylaromatic precursor with an oxygen-containing gas in the presence of a first catalyst comprising a cyclic imide having a general formula (III):

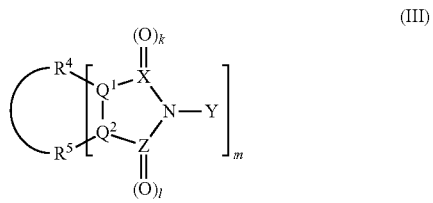

wherein each of $R^4$ and $R^5$ is independently selected from hydrocarbyl and substituted hydrocarbyl radicals having 1 to 20 carbon atoms, or from the groups $SO_3H$, $NH_2$, $OH$, and $NO_2$ or from the atoms H, F, Cl, Br, and I, provided that $R^4$ and $R^5$ can be linked to one another via a covalent bond; each of $Q^1$ and $Q^2$ is independently selected from C, CH, N, $CR^6$; each of X and Z is independently selected from C, S, $CH_2$, N, P and elements of Group 4 of the Periodic Table of Elements; Y is O or OH; k is 0, 1, or 2; l is 0, 1, or 2; m is 1 to 3; and $R^6$ can be any of the entities listed for $R^4$, and wherein said contacting is conducted under conditions to convert the alkylaromatic compound to the desired hydroperoxide.

Conveniently, the cyclic imide of the first catalyst has the general formula (IV):

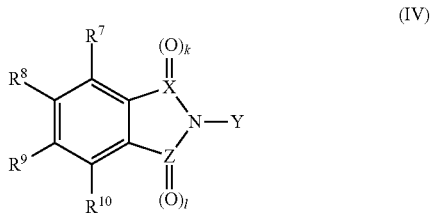

wherein each of $R^7$, $R^8$, $R^9$, and $R^{10}$ is independently selected from hydrocarbyl and substituted hydrocarbyl radicals having 1 to 20 carbon atoms, or from the groups $SO_3H$, $NH_2$, OH, and $NO_2$ or from the atoms H, F, Cl, Br, and I, each of X and Z is independently selected from C, S, $CH_2$, N, P and elements of Group 4 of the Periodic Table of Elements; Y is O or OH; k is 0, 1, or 2; and l is 0, 1, or 2.

In one embodiment, the cyclic imide comprises N-hydroxyphthalimide ("NHPI").

In another embodiment, the oxidation reaction is conducted with a cyclic imide in the absence of an additional radical initiator such as azobisisobutyronitrile (AIBN).

Suitable conditions for the oxidation step include a temperature between about 70° C. and about 200° C., such as about 90° C. to about 130° C., and a pressure of about 0.5 to about 20 atmospheres (50 to 2000 kPa). In one embodiment, the oxidation reaction is conveniently conducted in a catalytic distillation unit. The per-pass conversion is kept below 50%, preferably in the range of 45-35%, and more preferably in the range 30-20%, to minimize the formation of byproducts. In a preferred embodiment, the oxidation reaction occurs in a first reactor separate from the cleavage reaction which takes place in a second reactor. The first reactor can be one or a series of reactors or two or more reactors in parallel. Additionally, the second reactor can also be one or a series of reactors or two or more reactors in parallel.

The oxidation step converts the alkylaromatic precursor compound to its associated hydroperoxide. However, the oxidation process also tends to generate water and organic acids (e.g., acetic or formic acid) as by-products, which can hydrolyze the catalyst and also lead to decomposition of the hydroperoxide species. Thus, in one embodiment, the conditions employed in the oxidation step, particularly the pressure and oxygen concentration, are controlled so as to maintain the concentration of water and organic acids in the reaction medium below 50 ppm. Such conditions typically include conducting the oxidation at relatively low pressure, such as below 300 kPa, for example between about 100 kPa and about 200 kPa. Moreover, although the oxidation can be conducted over a broad oxygen concentration range between 0.1 and 100%, it is preferred to operate at relatively low oxygen concentration, such as no more than 21 volume %, for example from about 0.1 to about 21 volume %, generally from about 1 to about 10 volume %, oxygen in the oxygen-containing gas. In addition, maintaining the desired low levels of water and organic acids is facilitated by passing a stripping gas through the reaction medium during the oxidation step. In one embodiment, the stripping gas is the same as the oxygen-containing gas. In another embodiment, the stripping gas is different from the oxygen-containing gas and is inert to the reaction medium and the cyclic imide catalyst. Suitable stripping gases include inert gases, such as helium and argon.

An additional advantage of operating the oxidation process at low pressure and low oxygen concentration and by stripping water and organic acids, from the reaction medium is that light hydroperoxide (e.g., ethyl or methyl hydroperoxide), light ketones (e.g., methyl ethyl ketone), light aldehydes (e.g., acetaldehyde) and light alcohols (e.g., ethanol) are removed from the reaction products as they are formed. Thus light hydroperoxides are hazardous and pose a safety concern if their concentration in the liquid product becomes too high. Also, light hydroperoxides, alcohols, aldehydes and ketones are precursors for the formation of organic acids and water so that removing these species from the oxidation medium improves the oxidation reaction rate and selectivity and the stability of the cyclic imide catalyst. In fact, data shows that when conducting oxidation of sec-butylbenzene with NHPI at 100 psig (790 kPa), more than 99 mol % of these light species and water remain in the reactor, whereas at atmospheric pressure, more than 95 mol % of these species are removed from the oxidation reactor.

The product of the oxidation reaction includes the desired alkyl hydroperoxide together with unreacted alkylaromatic compound precursor and cyclic imide catalyst. However, as will be discussed below, the cyclic imide catalyst and their decomposition products (acids and ethers) can act as a poison to the downstream reactions, such as hydroperoxide cleavage. Moreover, the cyclic imide tends to be expensive, making it desirable to remove and/or recover and recycle the first catalyst. Thus, it will normally be desirable to treat the effluent stream from the oxidation process to remove at least part of the cyclic imide of the first catalyst prior to passage of the effluent stream to the cleavage of the hydroperoxide. In a preferred embodiment, the cyclic imide is removed in a separate vessel that is downstream of the first oxidation reactor and upstream of the second cleavage reactor. The product of the oxidation reactor may also include phenylcyclohexanone as well as phenylcyclohexanol. In the cleavage reactor, at least part of the cyclohexanone may be converted to phenylcyclohexene and at least part of the phenylcyclohexanol may be converted to phenylcyclohexene.

In one embodiment, treatment of the oxidation effluent stream to remove at least part of the cyclic imide comprises contacting the effluent stream with an aqueous solution of a base, particularly a weak base having a pKb value greater than or equal to the pKa of the cyclic imide of the first catalyst, whereby the imide is extracted into the aqueous phase, leaving an organic phase which comprises said oxidized hydrocarbon product and which contains a reduced level of cyclic imide. Generally, the extraction is conducted so as to reduce the level of the imide in the organic phase to less than 100 ppm, such as less than 50 ppm, for example less than 10 ppm, by weight of the organic phase, while the alkylaromatic hydroperoxide of the treated effluent stream is not substantially concentrated.

The use of a weak base in the extraction of the imide of the first catalyst is generally desirable since a weak base is less likely to catalyze decomposition of the imide after extraction into the aqueous phase. A suitable weak base includes a metal carbonate and/or hydrogen carbonate, especially an alkali metal carbonate and/or hydrogen carbonate, such as sodium carbonate.

The conditions used in the cyclic imide extraction step need not be closely controlled but generally include a temperature of about 10° C. to about 80° C., such as about 20° C. to about 70° C. The time of extraction may be for example from about 1 minute to about 30 minutes, such as about 5 minutes to about 10 minutes. The amount of base employed in the extraction step is normally sufficient to provide at least an equimolar quantity of base to imide, such as 1 to 3 moles of base per mole of cyclic imide. Generally, the phases are agitated during extraction to maximize contact between the phases.

After extraction into the aqueous base solution, the cyclic imide of the first catalyst may be readily recovered by acidifying the aqueous phase, for example with acetic acid, to precipitate the imide. After separation from the aqueous phase, for example by filtration or centrifugation, the precipitated imide may, if desired, be recycled to the oxidation step.

In another embodiment, treatment of the oxidation effluent to remove at least part of the cyclic imide comprises contacting the effluent with an effective solid sorbent, so as to produce a treated effluent stream in which alkylaromatic hydroperoxide is not substantially concentrated and which contains a reduced or zero level of cyclic imide. Again, the sorption process is conducted so as to reduce the level of the imide in the organic phase to less than 100 ppm, such as less than 50 ppm, for example less than 10 ppm, of the organic phase.

Suitable solid sorbents are those having basic properties, including metal carbonates and/or hydrogen carbonates, which may be provided on a porous support, clays, ion exchange resins and metal oxides, particularly mixed metal oxides.

Metal oxides having sufficient basic properties to be effective sorbents in the cyclic imide extraction step may be determined by the molar ratio of chemisorption of $CO_2$ and $NH_3$ over these metal oxide materials. $CO_2$, a mild acid, is used to titrate the basic sites present on the metal oxide being tested. Likewise, $NH_3$, a strong base, is titrated to indicate the acidic sites on the material. Many factors determine the actual amount of chemisorption such as surface area of the material (often significantly affected by the metal oxide preparation method), the temperature at which the chemisorption is tested, and the pressure at which the chemisorption is tested. For the present purposes, a "basic" oxide is defined as an oxide having a molar ratio of chemisorption of $CO_2$ per gram of metal oxide to the chemisorption of $NH_3$ per gram of metal oxide greater than 0.5, typically greater than 0.75, and especially greater than 1.0, when tested as described below.

Testing to determine the molar ratio of chemisorption of $CO_2$ per gram of metal oxide to the chemisorption of $NH_3$ per gram of metal oxide is conducted using a Mettler TGA/SDTA 851 thermogravimetric analysis system at ambient pressure. The metal oxide sample is calcined in flowing air to about 500° C. (except as noted in Table 1) for about three hours; at least until a constant sample weight is obtained. The temperature of the sample is then reduced in flowing air (helium could also be used) to the desired temperature of chemisorption. Next, the sample is allowed to equilibrate at the desired temperature in flowing helium and weighed. Chemisorption of carbon dioxide is measured at 100° C., and chemisorption of ammonia is measured at 250° C. After being weighed, the sample is subjected to a number of pulses (about 12 seconds/pulse) of gaseous mixture containing helium and either carbon dioxide or ammonia until a constant weight was obtained. The gas mixture contains about 10 weight percent carbon dioxide or ammonia with the remainder being helium. After each pulse of the gas mixture being tested, the metal oxide sample is flushed with flowing helium for about 3 minutes. About 20 separate pulses of the gas mixture is used in each test. The increase in weight of the sample in terms of mg/g metal oxide based on the metal oxide sample weight after calcination is used to determine the moles of $CO_2$ or $NH_3$ adsorbed per gram of metal oxide.

Molar ratios of chemisorption of $CO_2$ to the chemisorption of $NH_3$ per gram of sorbate for some representative metal oxide species are shown in Table 1.

TABLE 1

| Material Tested | Calcination Temperature, ° C. | $CO_2/NH_3$ Chemisorption Molar Ratio |
|---|---|---|
| $TiO_2$ | 700 | 0.33 |
| $W/ZrO_2$ | 800 | 0.07 |
| $La_2O_3$ | 700 | 0.86 |
| $La/SiO_2$ | 500 | 0.92 |
| $AlPO_x$ | 500 | 0.75 |
| $NdAlPO_x$ | 500 | 1.04 |
| $YAlPO_x$ | 500 | 0.86 |
| $PrAlPO_x$ | 500 | 1.05 |
| MgO | 700 | 11.47 |
| $Y_2O_3$ | 700 | 14.95 |

Metal oxides suitable for use as solid sorbents in the cyclic imide extraction step include oxides and mixed oxides of metals of Group 2, Group 3, Group 4, Lanthanide Series, or Actinide Series of the Periodic Table of Elements. In one embodiment, the sorbent comprises two or more metal oxides, preferably one Group 4 metal oxide and one or more selected from Group 2, Group 3, Lanthanide Series, and Actinide Series metal oxides. The oxides can be prepared using a variety of methods, although generally are prepared by conversion of a suitable precursor by precipitation from solution and/or calcination. Suitable precursors include metal salts, such as halides, sulfates, phosphates, halides, nitrates, oxychlorides, alkoxides and acetates.

In one embodiment, the metal oxide is produced by first preparing a liquid solution comprising a salt of the metal in a solvent, such as water. The resultant solution is then subjected to conditions sufficient to cause precipitation of the solid oxide material, such as by the addition of a precipitating reagent, typically a base such as sodium hydroxide or ammonium hydroxide. The liquid solution is generally maintained at a temperature at or below 200° C. during the precipitation, for example in the range of from about 0° C. to about 200° C., such as from about 20° C. to about 100° C. The resulting gel is preferably then hydrothermally treated at a temperature of at least 80° C., preferably at least 100° C., for up to 10 days, such as up to 5 days, for example up to 3 days. The resulting material is then recovered, for example by filtration or centrifugation, washed, and dried. The resulting particulate material is typically then calcined, normally in an oxidizing atmosphere, at a temperature of at least 400° C., such as from about 400° C. to about 800° C., for up to 48 hours, such as for about 0.5 hours to about 24 hours, for example for about 1 hour to about 10 hours.

When two or more metal oxides are used in the cyclic imide extraction step, they may either be co-precipitated or precipitated separately and combined with each other at any later stage of processing including as calcined solid particles.

Suitable ion exchange resins for use as the solid sorbent include those resins conventionally employed for removing acidic or basic species, such as Amberlyst exchange resins.

Suitable conditions for the cyclic imide sorption with a solid sorbent include a temperature of about 10° C. to about 130° C., such as about 20° C. to about 80° C., for a time of about 1 minute to about 30 minutes, such as about 5 minutes to about 10 minutes.

After removal by the solid sorbent, the cyclic imide can readily be recovered by washing the sorbent with a polar solvent, for example with ethanol or acetone. The recovered imide can then be recycled to the oxidation step, with or without prior removal of the ethanol, since it is found that the presence of ethanol with the imide does not adversely affect the oxidation activity or selectivity of the recycled first catalyst.

Hydroperoxide Cleavage

The hydroperoxide cleavage step of the present process is conducted by contacting at least a portion of the treated or untreated effluent stream from the oxidation step, normally after removal of the unreacted alkylaromatic precursor to concentrate the alkylaromatic hyroperoxides in the effluent stream above 50 wt %, 60 wt %, 70 wt %, 80 wt %, or 90 wt %, and optionally after pretreating the effluent stream to reduce the level of cyclic imide to less than 100 ppm, with a second catalyst.

It has been unexpectly found that the cleavage reaction is more efficient when the oxidation effluent has a concentration of 40 wt % or less of alkylaromatic hyroperoxides. In one embodiment, the oxidation effluent stream will have an alkylaromatic hydroperoxide concentration of from 1 to 40 wt %; from 5 to 35 wt %; from 10 to 30 wt %, from 10 to 25 wt %; and from 15 to 25 wt %. It is preferred that the oxidation reactor be operated to produce an oxidation effluent within these alkylaromatic hydroperoxide concentration ranges, and it is preferred that the oxidation effluent not be substantially concentrated prior to introducing the oxidation effluent into the cleavage reactor. In one embodiment, the alkylaromatic hydroperoxide is cumene hydroperoxide. In another embodiment, the alkylaromatic hydroperoxide is sec-butyl benzene hydroperoxide. In still another embodiment, the alkylaromatic hydroperoxide is cyclohexylbenzene hydroperoxide.

In other embodiments, the oxidation effluent stream may have a lower alkylaromatic hydroperoxide concentration of from 1 wt %, 5 wt %, 10 wt %, 12.5 wt %, 15 wt %, 17.5 wt %, and 20 wt %; and the upper alkylaromatic hydroperoxide concentration may be 22.5 wt %, 25 wt %, 27.5 wt %, 30 wt %, 32.5 wt %, 35 wt %, 37.5 wt %, and 40 wt % with ranges from any lower concentration to any upper concentration being contemplated.

In one embodiment, the alkyaromatic hydroperoxide is not substantially concentrated in the effluent stream prior to introducing the effluent stream or at least a portion of the effluent stream to the cleavage reactor. "Not substantially concentrated" is generally defined as maintaining the concentration of the alkyaromatic hydroperoxide in the oxidation effluent stream fed to the cleavage reactor within a 10% range of the original alkyaromatic hydroperoxide concentration in the oxidation effluent stream exiting the oxidation reactor. For illustration purposes only, if the alkyaromatic hydroperoxide concentration of the oxidation effluent stream exiting the oxidation reactor is 20 wt %, then the alkyaromatic hydroperoxide peroxide will be concentrated to no more than 22 wt % prior to introducing the effluent stream or at least a portion of the effluent stream to the cleavage reactor for the effluent stream to be considered "not substantially concentrated."

In another embodiment, the alkyaromatic hydroperoxide is not materially concentrated in the effluent stream prior to introducing the effluent stream or at least a portion of the effluent stream to the cleavage reactor. "Not materially concentrated" is generally defined as maintaining the concentration of the alkyaromatic hydroperoxide in the oxidation effluent stream entering the cleavage reactor within a 5% range of the original alkyaromatic hydroperoxide concentration in the oxidation effluent stream leaving the oxidation reactor. For illustration purposes only, if the alkyaromatic hydroperoxide concentration of the oxidation effluent stream is 20 wt %, then the alkyaromatic hydroperoxide peroxide will be concentrated to no more than 21 wt % prior to introducing the effluent stream in the cleavage reactor for the effluent stream to be considered "not materially concentrated."

In still another embodiment, the alkyaromatic hydroperoxide is not essentially concentrated in the effluent stream prior to introducing the effluent stream or at least a portion of the effluent stream to the cleavage reactor. "Not essentially concentrated" is generally defined as maintaining the original concentration of the alkyaromatic hydroperoxide in the oxidation effluent stream leaving the oxidation reactor so that the original alkyaromatic hydroperoxide concentration is essentially the same as the alkyaromatic hydroperoxide concentration of the oxidation effluent stream entering the cleavage reactor.

In another embodiment, the alkyaromatic hydroperoxide concentration in the effluent stream is "not concentrated" so that the alkyaromatic hydroperoxide concentration being introduced into the cleavage reactor is within a 2 wt % range of the original alkyaromatic hydroperoxide concentration in the effluent stream exiting the oxidation reactor. In still another embodiment, the alkylaromatic hydroperoxide concentration in the effluent stream may be diluted prior to introducing the effluent stream into the cleavage reactor such as by a recycle stream.

In another embodiment, no more than 10% of said alkylaromatic compound in the effluent stream exiting the oxidation reactor is removed from said effluent stream prior to introducing the effluent stream to the cleavage reactor. In still another embodiment, no more than 2.5%, or no more than 5% or no more than 15% or no more than 20% or no more than 25% of said alkylaromatic compound in the effluent stream exiting the oxidation reactor is removed from said effluent stream prior to introducing the effluent stream to the cleavage reactor The process of any one of the preceding claims wherein none of said alkylaromatic compound is removed from said effluent stream prior to said contacting (c).

The second catalyst is selected from the group consisting of a homogenous catalyst, a heterogeneous catalyst and mixtures thereof. The catalyst employed in the cleavage step can be a homogeneous catalyst or a heterogeneous catalyst.

Suitable homogeneous cleavage catalysts include acidic catalytic compounds such as sulfuric acid, perchloric acid, phosphoric acid, hydrochloric acid and p-toluenesulfonic acid. Ferric chloride, boron trifluoride, sulfur dioxide and sulfur trioxide are also effective homogeneous cleavage catalysts. The preferred homogeneous cleavage catalyst is sulfuric acid, with preferred concentrations in the range of 0.05 to 0.5 wt %. The cleavage reaction can be carried out in either a continuously stirred tank reactor (CSTR) or a batch reactor, with or without a co-solvent. Suitable co-solvents include acetone, methyl ethyl ketone, cyclohexanone, acetonitrile, nitromethane, and mixtures thereof. Also suitable as a co-solvent is a phenol/cyclohexylbenzene mixture containing 1-10% of phenol. Sulfuric acid used can either be in concentrated (96-98%) form or in dilute form (5-50% in a suitable solvent such as nitromethane). Cleavage reaction is carried out in the temperature range of 20-200° C. and a pressure of ambient to 200 psig. Residence time of 0.5-30 min is preferred for high conversion of hydroperoxide and good selectivity to cleavage products. When sulfuric acid is used as a homogeneous acid catalyst, a neutralization step normally follows the cleavage step. Such a neutralization step typically involves contact with a basic component, such as sodium carbonate or sodium phenylate, with subsequent settling and decanting for removal a salt-enriched aqueous phase. Alternatively, neutralization can be realized using stoichiometric amount of organic amines such as aniline, substituted anilines, diisopropylamine, triethylamine, etc.

Suitable heterogeneous catalysts for use in the cleavage of alkylaromatic hydroperoxide include smectite clays, such as an acidic montmorillonite silica-alumina clay, as described in U.S. Pat. No. 4,870,217, acidic ion-exchange resins (e.g., Amberlyst 15), and aluminum chloride.

Suitable heterogeneous catalysts include a mixed metal oxide catalyst. In some embodiments, the mixed metal oxide catalyst comprises one or more of an oxide of at a metal from Groups 3 to 5 and Groups 7 to 14 of the Periodic Table of the Elements. In other embodiments, the heterogeneous catalysts further comprise an oxide of at least one metal from Groups 8 to 11 of the Periodic Table of the Elements, such as an oxide of iron and/or copper. In still other embodiments, the mixed metal oxide catalyst includes an oxide of at least one metal from Group 4 of the Periodic Table of the Elements and an oxide of at least one metal from Group 6 of the Periodic Table of the Elements. In preferred embodiments, the mixed metal oxide catalyst comprises zirconium oxide and an oxide of molybdenum and/or tungsten, e.g., acidic mixture of metal oxides ($WO_3/ZrO_2$, $MoO_3/ZrO_2$, etc.).

In one embodiment, the mixed metal oxide catalyst is conveniently prepared by combining a first liquid solution, such as an aqueous solution, comprising a source of ions of at least one metal from Groups 3 to 5 and Groups 7 to 14 with a second liquid solution, again such as an aqueous solution, comprising a source of ions of at least one Group 4 metal and optionally with a third solution comprising a source of ions of at least one Group 8 to 11 metal. This combination can take place under conditions sufficient to cause co-precipitation of a mixed oxide material as a solid from the liquid medium. Alternatively, the source of ions of the metal(s) from Groups 3 to 5 and Groups 7 to 14, the source of ions of the Group 4 metal and optionally the source of ions of the Group 8 to 11 metals may be combined into a single solution. This solution may then be subjected to conditions sufficient to cause co-precipitation of the solid mixed oxide material, such as by the addition of a precipitating reagent to the solution. Conveniently, the precipitation is conducted at a pH above 7. For example, the precipitating agent may be a base such as sodium hydroxide or ammonium hydroxide.

The temperature at which the liquid medium is maintained during the precipitation is generally less than about 200° C., such as in the range of from about 0° C. to about 200° C. A particular range of temperatures for precipitation is from about 20° C. to about 100° C. The resulting gel is preferably then hydrothermally treated at temperatures of at least 80° C., preferably at least 100° C. The hydrothermal treatment typically takes place in a vessel at atmospheric pressure. The gel, in one embodiment, is hydrothermally treated for up to 10 days, such as up to 5 days, for example up to 3 days.

The hydrated precursor to the mixed metal oxide is then recovered, for example by filtration or centrifugation, and washed and dried. The resulting material can then be calcined, such as in an oxidizing atmosphere, at a temperature of at least 400° C., such as at least 500° C., for example from about 600° C. to about 900° C., and particularly from about 650° C. to about 800° C., to form the mixed metal oxide catalyst. The calcination time is typically up to 48 hours, such as for about 0.5 to 24 hours, for example for about 1.0 to 10 hours. In one embodiment, calcination is carried out at about 700° C. for about 1 to about 3 hours.

The cleavage reaction is conveniently affected by contacting the hydroperoxide with the mixed metal oxide catalyst at a temperature of about 20° C. to about 150° C., such as about 40° C. to about 120° C., and/or a pressure of about 50 to about 2500 kPa, such as about 100 to about 1000 kPa and/or a liquid hourly space velocity (LHSV) based on the hydroperoxide of about 0.1 to about 1000 $hr^{-1}$, preferably about 1 to about 50 $hr^{-1}$. The cleavage reaction is conveniently conducted in a catalytic distillation unit.

The hydroperoxide is typically diluted in an organic solvent inert to the cleavage reaction, such as methyl ethyl ketone, phenol, cyclohexylbenzene, cyclohexanone and sec-butylbenzene, to assist in heat removal. More preferably, alkylaromatic hydroperoxide is dissolved in a polar solvent, such as acetone, for the cleavage reaction since it is found that the presence of the polar solvent can mitigate the poisoning of the mixed metal oxide catalyst cleavage catalyst by cyclic imides remaining from the oxidation reaction.

Irrespective of the presence or absence of cyclic imide in the effluent stream fed to the cleavage reaction it is found that the mixed metal oxide will tend to lose its activity over time, resulting in a decrease in the degree of conversion of the hydroperoxide to phenol. It is, however, found that the cleavage activity of the catalyst can be restored by periodically rejuvenating the catalyst by washing the catalyst with a polar solvent, such as acetone.

The hydroperoxide cleavage reaction of the present invention is highly effective. In the cleavage of the alkylaromatic hydroperoxide, the phenol yield is greater than or equal to about 0.90, preferably greater than or equal to about 0.93, more preferably greater than or equal to about 0.96, most preferably greater than or equal to about 0.98. With respect to the co-product produced, the co-product yield is greater than or equal to about 0.90, preferably greater than or equal to about 0.93, more preferably greater than or equal to about 0.96, most preferably greater than or equal to about 0.98.

"Yield" of a particular product is defined as the molar amount of product produced, divided by the total molar amount of corresponding hydroperoxide consumed during the reaction. For example, "phenol yield" for phenol from cyclohexylbenzene hydroperoxide (CHBHP) is the molar amount of phenol produced divided by the molar amount of cyclohexylbenzene hydroperoxide consumed in the cleavage reaction.

Where the alkylaromatic compound that is oxidized according to the invention is cumene, the alkylaromatic hydroperoxide product comprises cumene hydroperoxide and the cleavage products comprise phenol and co-product acetone. In this case, the acetone yield is greater than or equal to about 0.90, preferably greater than or equal to 0.93, more preferably greater than or equal to 0.96, most preferably greater than or equal to 0.98.

Where the alkylaromatic compound comprises sec-butylbenzene, the alkylaromatic hydroperoxide product according to the invention comprises sec-butylbenzene hydroperoxide and the cleavage products comprise phenol and co-product methyl ethyl ketone. In this case, the methyl ethyl ketone yield is greater than or equal to about 0.90, preferably greater than or equal to 0.93, more preferably greater than or equal to 0.96, most preferably greater than or equal to 0.98.

Where the alkylaromatic compound comprises cyclohexylbenzene, the alkylaromatic hydroperoxide product according to this invention comprises cyclohexylbenzene hydroperoxide and the cleavage product comprises phenol and co-product cyclohexanone. In this case, the cyclohexanone yield is greater than or equal to about 0.90, preferably greater than or equal to 0.93, more preferably greater than or equal to 0.96, most preferably greater than or equal to 0.98.

The crude phenol and the crude co-product, (e.g., acetone, methyl ethyl ketone, cyclohexanone) from the cleavage step may be subjected to further purification to produce purified phenol and co-product. A suitable purification process includes, but is not limited to, a series of distillation towers to separate the phenol and co-product from other species. Any of the crude or purified co-products, for example cyclohexanone, may itself be subjected to dehydrogenation in order to convert it to the corresponding alcohol, for example phenol. Such dehydrogenation may be performed, for example, over a catalyst such as platinum, nickel or palladium.

The invention will now be more particularly described with reference to the following non-limiting Examples.

Example 1

Oxidation of Cumene Using N-Hydroxyphthalimide (NHPI)

One hundred fifty grams of cumene from TCI America and 0.16 g NHPI from TCI were weighed into a Parr reactor fitted with a stirrer, thermocouple, gas inlet, sampling port and a condenser containing a Dean Stark trap for water removal. The reactor contents were stirred at 1000 rpm and sparged with nitrogen at a flow rate of 250 cc/minute for 5 minutes. The reactor, while maintained under a nitrogen sparge, was then heated to 115° C. When the reaction temperature was reached, the gas was switched from nitrogen to air and the reactor was sparged with air at 250 cc/minute for 4 hours. Samples were taken hourly and analyzed by gas chromatography (GC). After 4 hours, the gas was switched back to nitrogen and the heat was turned off.

Example 2

Sulfuric Acid Catalyzed Cleavage of Dilute Cumene Hydroperoxide (CHP)

Cumene oxidation products (including cumeme hyroperoxide, CHP) from Example 1 where NHPI was used as the first catalyst was used (containing 19.8% CHP, 77.6% cumene, 1.1% acetophenone, and 0.9% cumyl alcohol). An amount of 5.0 milliliters of such feed was charged into a glass flask held at 54° C. To this feed was added 0.5 milliliters of 1.5 wt. % sulfuric acid in nitromethane, giving a sulfuric acid concentration of 1600 ppm. Cleavage reaction occurred instantaneously as indicated by the reaction exotherm. An aliquot was taken after 15 min and sulfuric acid was neutralized using 10 wt. % sodium carbonate solution. The sample was analyzed by GC. Complete conversions for CHP and cumyl alcohol were achieved and only a small amount (0.6 wt. %) of heavy product cumyl phenol (alkylation products of α-methylstyrene with phenol) was observed.

Example 3

Oxidation of Sec-Butyl Benzene Using N-Hydroxyphthalimide (NHPI)

One hundred fifty grams of sec-butyl benzene (SBB) from TCI America and 0.16 g NHPI from TCI were weighed into a Parr reactor fitted with a stirrer, thermocouple, gas inlet, sampling port and a condenser containing a Dean Stark trap for water removal. The reactor contents were stirred at 1000 rpm and sparged with nitrogen at a flow rate of 250 cc/minute for 5 minutes. The reactor, while maintained under a nitrogen sparge, was then heated to 125° C. When the reaction temperature was reached, the gas was switched from nitrogen to air and the reactor was sparged with air at 250 cc/minute for 4 hours. Samples were taken hourly and analyzed by gas chromatography. After 4 hours, the gas was switched back to nitrogen and the heat was turned off.

Example 4

Sulfuric Acid Catalyzed Cleavage of Dilute Sec-Butyl Benzene Hydroperoxide (SBBHP)

sec-Butyl benzene oxidation products (including sec-butyl benzene hydroperoxide, SBBHP) from Example 3 where NHPI was used as the first catalyst was used (containing 17.2% SBBHP, 79.1% sec-butyl benzene, 1.99% acetophenone, and 0.85% methyl ethyl benzyl alcohol). An amount of 5.0 milliliters of such feed was charged into a glass flask held at 54° C. This feed was added 0.5 milliliters of 1.5 wt. % sulfuric acid in nitromethane, giving a sulfuric acid concentration of 1600 ppm. Cleavage reaction occurred instantaneously as indicated by the reaction exotherm. An aliquot was taken after 15 min and sulfuric acid was neutralized using 10 wt. % sodium carbonate solution. The sample was analyzed by GC: complete conversions for SBBHP and methyl ethyl benzyl alcohol were achieved and no heavy product was observed.

Example 5

Oxidation of Cyclohexyl Benzene (CHB) Using N-Hydroxyphthalimide

One hundred fifty grams of cyclohexyl benzene from TCI America and 0.16 g NHPI from TCI were weighed into a Parr reactor fitted with a stirrer, thermocouple, gas inlet, sampling port and a condenser containing a Dean Stark trap for water removal. The reactor contents were stirred at 1000 rpm and sparged with nitrogen at a flow rate of 250 cc/minute for 5 minutes. The reactor, while maintained under a nitrogen sparge, was then heated to 110° C. When the reaction temperature was reached, the gas was switched from nitrogen to air and the reactor was sparged with air at 250 cc/minute for 4 hours. Samples were taken hourly and analyzed by gas chromatography. After 4 hours, the gas was switched back to nitrogen and the heat was turned off.

Example 6

Sulfuric Acid Catalyzed Cleavage of Dilute Cyclohexylbenzene Hydroperoxide

Cyclohexylbenzene oxidation products (including cyclohexylbenzene hydroperoxide, CHBHP) from Example 5 where NHPI was used the first catalyst was used. An amount of 5.0 milliliters of such feed was charged into a glass flask held at 53° C. and decane was added as an internal standard. Toward this feed was added 0.5 milliliters of 1.5 wt. % sulfuric acid in nitromethane, giving a sulfuric acid concentration of 1600 ppm. Cleavage reaction occurred instantaneously as indicated by the reaction exotherm. An aliquot was taken after 10 min and sulfuric acid was neutralized using 10 wt. % sodium carbonate solution. The sample was analyzed by GC and the results are listed in Table 2. High conversion of CHBHP was observed and no by-product formation was observed.

Example 7

Concentrating CHBHP from CHB Oxidation Products by Rotary Evaporation Under Vacuum The NHPI contained in the CHB oxidation products (e.g., CHBHP) was removed by washing with 1% sodium carbonate solution. The organic layer was concentrated by rotary evaporation under 1-2 mm vacuum and at 90-92° C. The concentration of CHBHP in the concentrated solution is about 48%.

TABLE 2

| Sulfuric acid catalyzed cleavage of dilute CHBHP | | |
|---|---|---|
| Component | Feed | Product |
| Cyclohexanone | 0.04 | 6.22 |
| Phenol | 0.03 | 6.15 |
| Decane | 8.20 | 8.20 |
| Ph-cyclohexene1 | 0.00 | 0.03 |
| C12H16 (MCPB) | 0.41 | 0.42 |
| Cyclohexylbenzene | 74.43 | 76.39 |

TABLE 2-continued

Sulfuric acid catalyzed cleavage of dilute CHBHP

| Component | Feed | Product |
|---|---|---|
| Ph-cyclohexene2 | 0.19 | 0.77 |
| 4-Ph-cyclohexanol | 0.74 | 0.32 |
| 1-Ph-cyclohexanol | 1.33 | 0.00 |
| Phcyclohexanones | 0.35 | 0.44 |
| CHBHP | 12.75 | 0.13 |
| Peroxide1 | 0.16 | 0.13 |
| peroxide2 | 0.05 | 0.00 |
| peroxide4 | 0.04 | 0.00 |
| 1-Ph-1,4-dihydroxylCH | 0.44 | 0.43 |
| Diperoxide | 0.15 | 0.15 |
| o-DiCyBz | 0.03 | 0.03 |
| m-DiCyBz | 0.05 | 0.05 |
| p-DiCyBz | 0.13 | 0.13 |
| Hi-oxygenates3 | 0.21 | 0.00 |
| Hi-oxygenates2 | 0.09 | 0.00 |
| Hi-oxygenates1 | 0.09 | 0.00 |
| Hi-oxygenates4 | 0.04 | 0.00 |
| CHBHP conv. | | 98.99 |
| Cyclohexanone yield | | 96.56 |
| PhOH yield | | 99.47 |

Example 8

Sulfuric Acid Catalyzed Cleavage of Concentrated CHBHP

The concentrated CHBHP generated in Example 7 was used. An amount of 5.0 milliliters of such feed was charged into a glass flask held at 20° C. To this feed was added 13 milliliters of concentrated sulfuric acid (96.6%), giving a sulfuric acid concentration of 5000 ppm. Cleavage reaction occurred instantaneously as indicated by the reaction exotherm. An aliquot was taken after 10 min and sulfuric acid was neutralized using 10 wt. % sodium carbonate solution. The sample was analyzed by GC and the results are listed in Table 3. High conversion of CHBHP was observed; but large amounts of light and heavy by-products were observed and the yields to cyclohexanone and phenol are low.

TABLE 3

Sulfuric acid catalyzed cleavage of concentrated CHBHP

| Component | Feed | Product |
|---|---|---|
| Pentanal | 0.00 | 0.12 |
| Cyclohexanone | 0.15 | 11.32 |
| Cyclohexenones | 0.00 | 0.64 |
| Phenol | 0.11 | 16.23 |
| 1-Hydroxyphenol | 0.00 | 1.03 |
| Cyclohexyl-1,2-diketone | 0.00 | 0.20 |
| Benzoic acid | 0.41 | 0.22 |
| Methylcyclopentylbenzene | 0.08 | 0.08 |
| CHB | 36.17 | 40.23 |
| Phenylcyclohexenes | 0.65 | 10.55 |
| 4-Phenylcyclohexanol | 2.83 | 4.94 |
| 1-Phenylcyclohexanol | 5.02 | 0.22 |
| Cyclohexanone aldol | 0.14 | 0.86 |
| Phenylcyclohexanone | 0.51 | 1.24 |
| CHBHP | 47.84 | 0.58 |
| Other peroxides | 1.72 | 0.61 |
| Phenyldihydroxylcyclohexane | 1.50 | 8.25 |
| Diperoxides | 0.55 | 0.82 |
| Heavies | 2.33 | 1.86 |
| CHBHP Conversion | | 98.79 |
| Phenol yield | | 70.16 |
| Cyclohexanone yield | | 46.93 |

As demonstrated in Examples 7 and 8, CHBHP from CHB oxidation can be concentrated by vacuum distillation at elevated temperatures. But the cleavage of the concentrated CHBHP proceeds much less cleanly as compared to diluted CHBHP. Large amounts of light and heavy by-products are formed and the yields to phenol and cyclohexanone are low when the CHBHP is concentrated. Clean cleavage reactions are also observed for diluted cumene hydroperoxide and sec-butylbenzene hydroperoxide. These findings show an advantageous embodiment of cleaving dilute hydroperoxides without first concentrating the hydroperoxides from the oxidation products.

Example 9

Sulfuric Acid Catalyzed Cleavage of Dilute Cyclohexylbenzene Hydroperoxide

Cyclohexylbenzene oxidation products (including cyclohexylbenzene hydroperoxide, CHBHP) using NHPI as the first catalyst with varying CHBHP concentrations are used (without first concentrating the hydroperoxide) in this example. An amount of 5.0 milliliters of such feed was charged into a glass flask held at 58° C. Toward this feed was added 5000 ppm of sulfuric acid diluted in acetone in a semi-batch mode. Cleavage reaction occurred instantaneously as indicated by the reaction exotherm. An aliquot was taken after 10 min and sulfuric acid was neutralized using 10 wt % sodium carbonate solution. The sample was analyzed by GC and the results are listed in Table 4. High conversion of CHBHP and high yield to phenol and cyclohexanone were observed in all cases.

TABLE 4

Sulfuric acid catalyzed cleavage of dilute CHBHP

| | Run # | | | | | |
|---|---|---|---|---|---|---|
| | A | | B | | C | |
| Component | Feed | Product | Feed | Product | Feed | Product |
| Cyclohexanone | 0.03 | 9.27 | 0.04 | 12.28 | 0.03 | 7.76 |
| Phenol | 0.04 | 9.43 | 0.04 | 12.59 | 0.02 | 7.89 |
| C12H16 (MCPB) | 4.28 | 4.34 | 3.80 | 3.85 | 4.70 | 4.72 |
| Cyclohexylbenzene | 70.19 | 71.10 | 62.37 | 62.90 | 75.00 | 75.19 |
| Ph-cyclohexene | 0.11 | 1.10 | 0.14 | 2.31 | 0.09 | 0.80 |
| 4-Ph-cyclohexanol | 0.19 | 0.18 | 0.37 | 0.36 | 0.16 | 0.12 |
| 1-Ph-cyclohexanol | 0.62 | 0.12 | 1.37 | 0.09 | 0.38 | 0.01 |
| Phcyclohexanones | 1.25 | 0.62 | 1.37 | 1.07 | 1.03 | 0.45 |
| CHBHP | 19.56 | 0.17 | 25.44 | 0.34 | 15.49 | 0.15 |
| Other peroxides | 1.03 | 0.28 | 1.64 | 0.42 | 0.79 | 0.12 |
| Diperoxide | 0.37 | 0.05 | 0.05 | 0.05 | 0.05 | 0.05 |
| o-DiCyBz | 0.01 | 0.01 | 0.01 | 0.01 | 0.01 | 0.01 |
| m-DiCyBz | 0.01 | 0.01 | 0.01 | 0.01 | 0.01 | 0.01 |
| p-DiCyBz | 0.02 | 0.02 | 0.02 | 0.02 | 0.02 | 0.02 |
| Other oxygenates | 0.20 | 0.68 | 0.47 | 0.90 | 0.13 | 0.30 |
| Other | 2.08 | 2.64 | 2.86 | 2.80 | 2.10 | 2.40 |
| CHBHP conv. | | 99.15 | | 98.68 | | 99.02 |
| Cyclohexanone yield | | 92.42 | | 95.04 | | 98.90 |
| PhOH yield | | 93.29 | | 97.98 | | 99.47 |

These examples clearly show that clean cleavage of cyclohexylbenzene hydroperoxide can be achieved when the products from the oxidation step are not concentrated. High yield to phenol and cyclohexanone is obtained. Preferred range of hydroperoxide concentration is 10 to 25%.

While the present invention has been described and illustrated by reference to particular embodiments, those of ordinary skill in the art will appreciate that the invention lends itself to variations not necessarily illustrated herein. For this reason, then, reference should be made solely to the appended claims for purposes of determining the true scope of the present invention.

The invention claimed is:

1. A continuous process for producing phenol or a substituted phenol and a co-product, the process comprising the steps of:

(a) contacting in a first reactor a first stream comprising an alkylaromatic compound with a second stream comprising an oxygen-containing gas in the presence of a first catalyst comprising a cyclic imide under conditions to convert at least a portion of said alkylaromatic compound to an alkylaromatic hydroperoxide, wherein said alkylaromatic compound having a general formula (II):

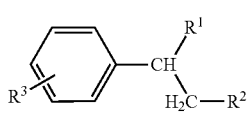
(II)

in which $R^1$ and $R^2$ each independently represents an alkyl group having from 1 to 4 carbon atoms, provided that $R^1$ and $R^2$ may be joined to form a cyclic group having from 4 to 10 carbon atoms, said cyclic group being optionally substituted, and $R^3$ represents hydrogen, one or more alkyl groups having from 1 to 4 carbon atoms or a cyclohexyl group, wherein said cyclic imide having a general formula (III):

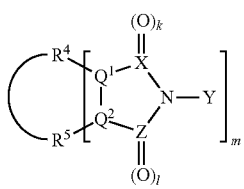
(III)

in which each of $R^4$ and $R^5$ is independently selected from hydrocarbyl and substituted hydrocarbyl radicals having 1 to 20 carbon atoms, or from the groups $SO_3H$, $NH_2$, $OH$, and $NO_2$ or from the atoms H, F, Cl, Br, and I, provided that $R^4$ and $R^5$ can be linked to one another via a covalent bond, each of $Q^1$ and $Q^2$ is independently selected from C, CH, N, $CR^6$, each of X and Z is independently selected from C, S, $CH_2$, N, P and elements of Group 4 of the Periodic Table of Elements, Y is O or OH, k is 0, 1, or 2, l is 0, 1, or 2;

m is 1 to 3; and $R^6$ can be any of the entities listed for $R^4$, and wherein said alkylaromatic hydroperoxide having a general formula (I):

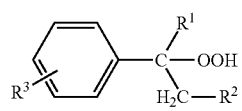
(I)

in which each of $R^1$, $R^2$ and $R^3$ is as defined above;

(b) producing an effluent stream comprising said cyclic imide, said alkylaromatic hydroperoxide, and said alkylaromatic compound wherein said effluent stream has an alkylaromatic hydroperoxide concentration of from 10 to 40 wt %; and (c) contacting in a second reactor at least a portion of said effluent stream with a second catalyst to convert said alkylaromatic hydroperoxide to a product stream comprising phenol and said co-product.

2. The process of claim 1, wherein said effluent stream has an alkyaromatic hydroperoxide concentration of from 10 to 30 wt %.

3. The process of claim 1, wherein said effluent stream has an alkyaromatic hydroperoxide concentration of from 10 to 25 wt %.

4. The process of claim 1, wherein the alkyaromatic hydroperoxide is not substantially concentrated in the effluent stream prior to said contacting (c).

5. The process of claim 1, wherein no more than 10% of said alkylaromatic compound is removed from said effluent stream prior to said contacting (c).

6. The process of claim 1, wherein said alkylaromatic compound is not removed from said effluent stream prior to said contacting (c).

7. The process of claim 1, wherein the phenol yield is greater than or equal to about 0.96.

8. The process of claim 1, wherein at least part of said cyclic imide is removed from said effluent stream prior to said contacting (c).

9. The process of claim 1, wherein said removing step (b) comprises removing at least part of said cyclic imide by contacting said effluent stream with a solid sorbent.

10. The process of claim 9, wherein said solid sorbent comprises at least one of a metal oxide, a metal carbonate and/or hydrogen carbonate, a clay, and/or an ion exchange resin.

11. The process of claim 1, wherein said cyclic imide having the general formula (IV):

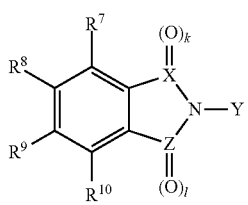
(IV)

wherein each of $R^7$, $R^8$, $R^9$, and $R^{10}$ is independently selected from hydrocarbyl and substituted hydrocarbyl radicals having 1 to 20 carbon atoms, or from the groups $SO_3H$, $NH_2$, OH, and $NO_2$ or from the atoms H, F, Cl, Br, and I, each of X and Z is independently selected from C, S, $CH_2$, N, P and elements of Group 4 of the Periodic Table of Elements, Y is O or OH, k is 0, 1, or 2, and l is 0, 1, or 2.

12. The process of claim 1, wherein said cyclic imide comprises N-hydroxyphthalimide.

13. The process of claim 1, wherein said second catalyst is selected from the group consisting of a homogenous catalyst, a heterogeneous catalyst and mixtures thereof.

14. The process of claim 1, wherein the second catalyst is an acidic catalyst selected from the group consisting of sulfuric acid, perchloric acid, phosphoric acid, hydrochloric acid and p-toluenesulfonic acid and mixtures thereof.

15. The process of claim 1, wherein said second catalyst is a heterogeneous catalyst comprising an oxide of at least one metal from Groups 3 to 5 and Groups 7 to 14 of the Periodic Table of the Elements and an oxide of at least one metal from Group 6 of the Periodic Table of the Elements.

16. The process of claim 1, wherein said second catalyst is a heterogeneous catalyst comprising an oxide of at least one metal from Group 4 of the Periodic Table of the Elements and an oxide of at least one metal from Group 6 of the Periodic Table of the Elements.

17. The process of claim 1, wherein said alkylaromatic compound is cumene, said alkylaromatic hydroperoxide is cumene hydroperoxide and said co-product is acetone.

18. The process of claim 1, wherein said alkylaromatic compound is sec-butylbenzene, said alkylaromatic hydroperoxide is sec-butylbenzene hydroperoxide and said co-product is methyl ethyl ketone.

19. The process of claim 1, wherein said alkylaromatic compound is cyclohexylbenzene, said alkylaromatic hydroperoxide is cyclohexylbenzene hydroperoxide and said co-product is cyclohexanone.

20. The process of claim 1, wherein said alkylaromatic compound is a compound chosen from cyclohexylbenzene, 1,2 methylcyclopentylbenzene and 1,3 methylcyclopentylbenzene wherein said alkylaromatic hydroperoxide is a compound chosen from cyclohexylbenzene hydroperoxide, 1,2 methylcylcopentylbenzene hydroperoxide, and 1,3 methylcylcopentylbenzene hydroperoxide, and said co-product is a compound chosen from cyclohexanone, 2 methylcyclopentanone, and 3 methylcyclopentanone.

21. The process of claim 1, wherein said oxygen-containing gas is atmospheric air.

22. The process of claim 1, wherein said cyclic imide is added to contacting step (a) in an amount of 0.001 wt % to 5 wt % of cyclic imide to said alkylaromatic compound.

23. The process of claim 1, wherein said effluent comprises phenylcyclohexanone and at least a portion of said phenylcyclohexanone is converted to phenylcyclohexene during said contacting (c).

24. The process of claim 1, wherein said effluent comprises phenylcyclohexanol and at least a portion of said phenylcyclohexanol is converted to phenylcyclohexene during said contacting (c).

25. A continuous process for producing phenol or a substituted phenol and cyclohexanone, the process comprising the steps of:
(a) contacting in a first reactor a first stream comprising cyclohexylbenzene with a second stream comprising air in the presence of a first catalyst comprising N-hydroxyphthalimide under conditions to convert at least a portion of said cyclohexylbenzene to cyclohexylbenzene hydroperoxide;
(b) producing an effluent stream comprising said N-hydroxyphthalimide, said cyclohexylbenzene hydroperoxide, and said cyclohexylbenzene wherein said effluent stream has a cyclohexylbenzene hydroperoxide concentration of from 10 to 40 wt %; and
(c) contacting in a second reactor at least a portion of said effluent stream with a second catalyst to convert said cyclohexylbenzene hydroperoxide to a product stream comprising phenol and cyclohexanone.

* * * * *